US012766025B2

(12) United States Patent
Charles

(10) Patent No.: US 12,766,025 B2
(45) Date of Patent: Oct. 20, 2026

(54) ORTHOPEDIC DEVICE AND METHOD OF USING SAME

(71) Applicant: George Charles, Belding, MI (US)

(72) Inventor: George Charles, Belding, MI (US)

( * ) Notice: Subject to any disclaimer, the term of this patent is extended or adjusted under 35 U.S.C. 154(b) by 0 days.

(21) Appl. No.: 19/220,725

(22) Filed: May 28, 2025

(65) Prior Publication Data

US 2026/0130784 A1 May 14, 2026

Related U.S. Application Data

(60) Provisional application No. 63/720,352, filed on Nov. 14, 2024.

(51) Int. Cl.
*A61F 5/00* (2006.01)
*A61F 5/02* (2006.01)

(52) U.S. Cl.
CPC .................................... *A61F 5/028* (2013.01)

(58) Field of Classification Search
CPC ........... A61F 5/026; A61F 5/028; A61F 5/024
USPC ............................................................ 602/19
See application file for complete search history.

(56) References Cited

U.S. PATENT DOCUMENTS 1,722,205 A * 7/1929 Freund .................... A61F 5/024 602/19
5,651,764 A * 7/1997 Chiu ....................... A61F 5/055 606/54
7,686,393 B2 * 3/2010 Rutty ..................... A47C 7/425 297/230.11
9,987,159 B2 * 6/2018 Williams ................ A61F 5/024
2015/0209213 A1 * 7/2015 Kline ................... A61H 1/0229 602/19
2023/0320887 A1 * 10/2023 Kimura ................... A61F 5/026 602/19

* cited by examiner

*Primary Examiner* — Kim M Lewis
(74) *Attorney, Agent, or Firm* — Mitchell Intellectual Property Law, PLLC

(57) ABSTRACT

An orthopedic device having a lateral under arm rest for positioning under a patient's arm, being supported by two spaced struts which extend downwardly and inwardly from their connection to the arm rest to their connection to housing which houses a fixed length outer sleeve which is mounted at its top in approximately the center of the under arm rest and at its bottom to the leg housing. The length of the fixed length sleeve is approximately the length of an upper torso from the underarms to the waist of a user. The fixed outer sleeve telescopically houses an inner telescoping sleeve of approximately the same length of the fixed length outer sleeve, but it can be adjustably telescoped out of the fixed length sleeve to change the effective length of the leg to accommodate use in a variety of orthopedic pain relief positions. In its uppermost position within the fixed length sleeve, it extends outwardly from the outer sleeve a short distance and has swivelly mounted on the outside of the telescoping sleeve near its terminal end a clip which can be clipped downwardly over a belt such that when the patient puts said under arm rest under his or her arm, his or her upper torso is stretched somewhat or partially unweighted.

9 Claims, 8 Drawing Sheets

ORTHOPEDIC DEVICE AND METHOD OF USING SAME

RELATED APPLICATION/PRIORITY BENEFIT CLAIM

This application claims priority to Provisional Application Ser. No. 63/720,352, filed Nov. 14, 2024, the content of which is incorporated herein by reference.

BACKGROUND OF THE INVENTION

The present invention relates to the field of lower back orthopedic pain devices and methods of treatment. Millions of people suffer with lower back pain which they treat with pain relief topical creams, aspirin, Tylenol and Advil. Usually, the pain persists and has to be continually addressed. Back braces are often used, but their effect is limited because they restrain movement of the patient and hold the patient in one position. Most people experience pain in varying different positions, often at different times.

Further, most back braces only provide relief within a very limited range of motion. This makes it difficult to "do life." Doing chores, laying down, sitting up, standing up, and lifting things becomes difficult. Further, doing such things aggravates the pain one wears the back rest to try and alleviate.

SUMMARY OF THE INVENTION

The present invention comprises an orthopedic device having a lateral under arm rest for positioning under a patient's arm; an adjustable length leg connected to and extending downwardly from said lateral under arm rest; and a swivelly mounted clip on the outside of said adjustable leg near its terminal end; said clip being configured to be clipped downwardly over a waist belt on a patient; said adjustable length leg being adjustable to extend approximately the length of a patient's upper torso from the underarm to the waist of a patient at a point where, when the patient puts said under arm rest under his or her arm, his or her upper torso is stretched somewhat or partially unweighted.

Because said clip is swivelly mounted, a patient can use it in a variety of relief giving positions, e.g., sitting, standing, laying down, standing, or laying on a side. Further, only one device might be used on one side of the body, or two of said devices can be used, one under each arm, in those various positions.

DESCRIPTION OF THE PREFERRED EMBODIMENTS

PARTS LIST for Orthopedic device 1

Figure 1:
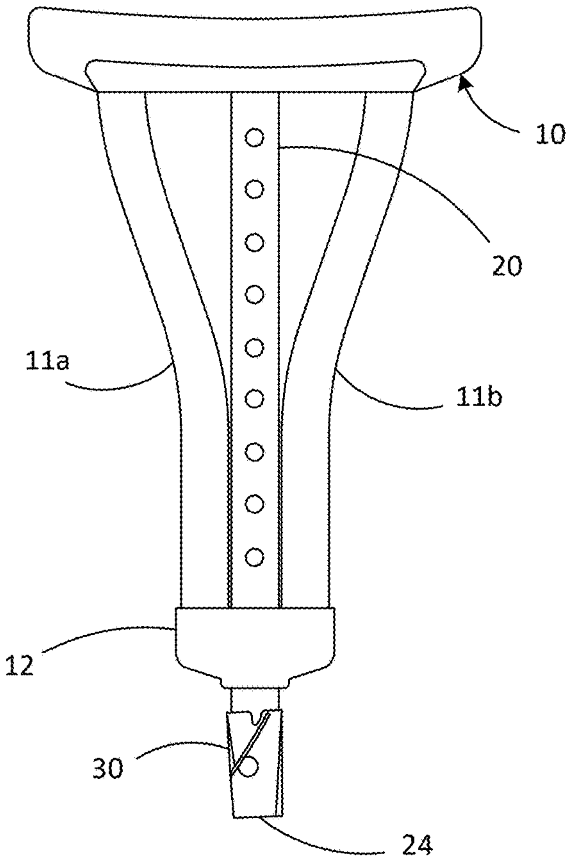
FIG. 1 is a plan view of orthopedic device 1 with adjustable leg in shortest length.

- Under arm rest 10
  - Strut 11*a*
  - Strut 11*b*
  - Leg housing 12
- Adjustable leg 20
  - Inner sleeve 21
- Spring biased adjustment button 21*a*
  - Outer sleeve 22
  - Adjustment openings 22*a*
  - Swivel clip mount 23
  - inner sleeve cap 24
- Swivel clip 30
  - Inner mounted leg 31
  - Outer spring clamping leg 32

Figure 2:
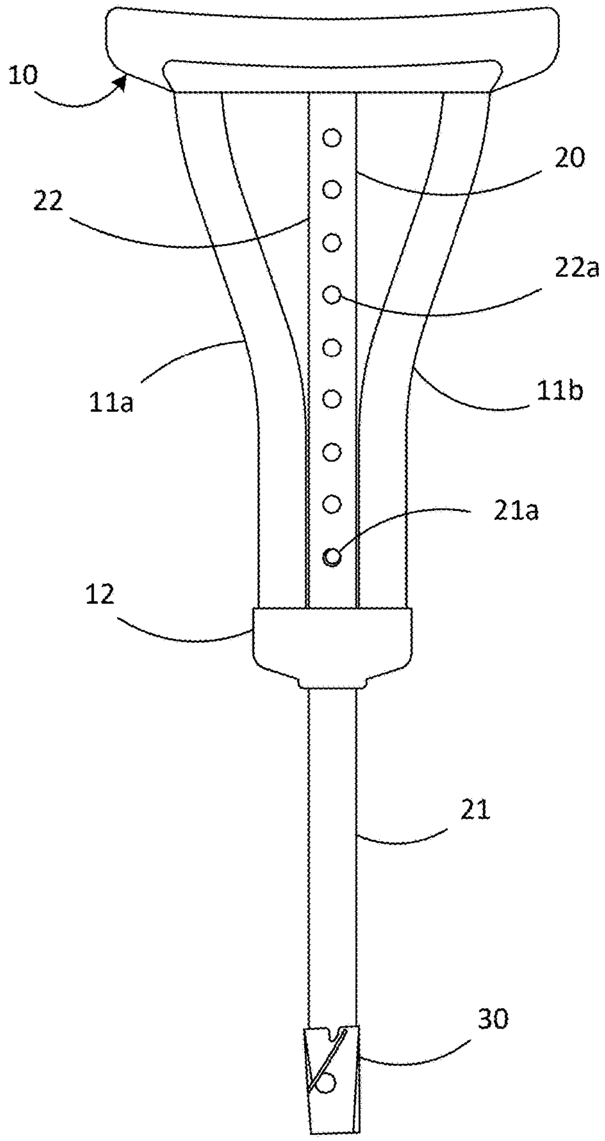
FIG. 2 is a plan view of orthopedic device with adjustable leg in extended length.

In the preferred embodiment, orthopedic device 1 has a lateral under arm rest 10 for positioning under a patient's arm. Under arm rest 10 is connected to two spaced struts 11*a* and 11*b*, which are connected to under arm rest 10 towards these spaced ends thereof. Struts 11*a* and 11*b* extend downwardly and inwardly from their connection to arm rest 10, to their connection to adjustable leg housing 12. Leg housing 12 houses adjustable leg 20. (FIGS. 1 & 2).

Figure 3:
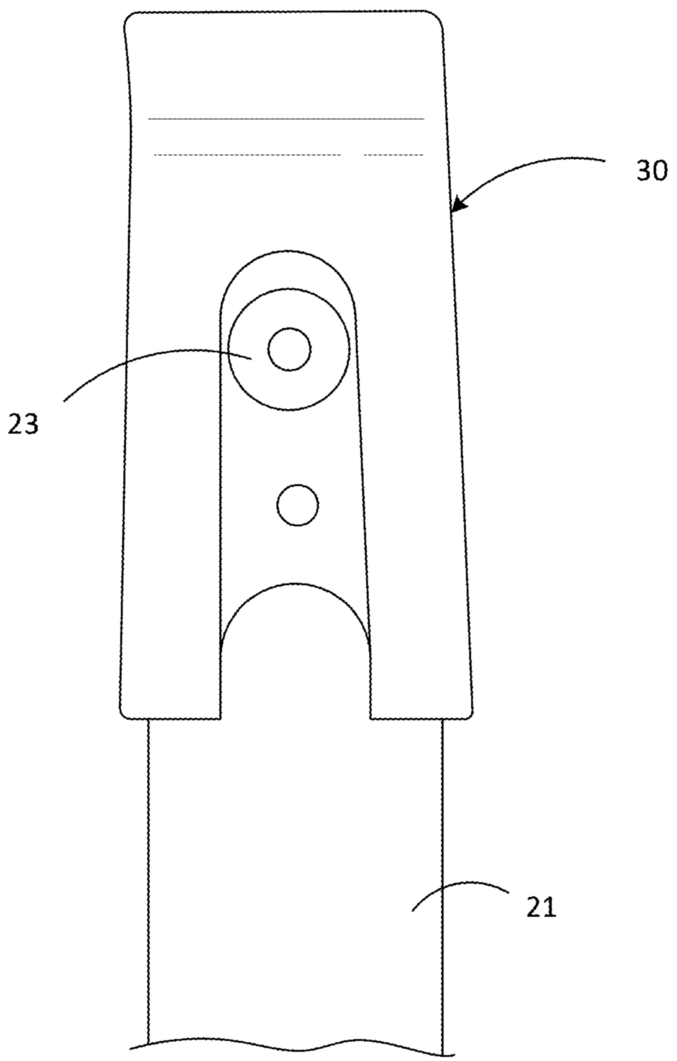
FIG. 3 is a plan view of swivel clip mounted on adjustable leg, shown in position parallel to leg.

Adjustable leg 20 comprises a fixed length outer sleeve 22 which is mounted at its upper end to and in approximately the center of under arm rest 10. At its bottom end, outer sleeve 22 is connected to leg housing 12. The length of fixed length outer sleeve 22 is approximately the length of a human body upper torso from the underarm to the waist of a user. This of course can vary from about ½ to about 1½ feet, with 1 foot being typical. The fixed outer sleeve 22 telescopically houses an inner telescoping sleeve 21 of approximately the same length of fixed length outer sleeve 22. It can be adjustably telescoped out of fixed length sleeve 22 to adjust the effective length of adjustable leg 20 to accommodate use for a variety of differing sized users in a variety of orthopedic pain relief positions. In its uppermost position within fixed length sleeve 22, inner sleeve 21 extends outwardly from the outer sleeve 22 a short distance, such that a swivelly mounted clip 30 is swivelly mounted on the outside of telescoping sleeve 21 near its terminal end, where it is capped with a cap end 24. (FIGS. 1, 2 & 3).

Figure 3A:
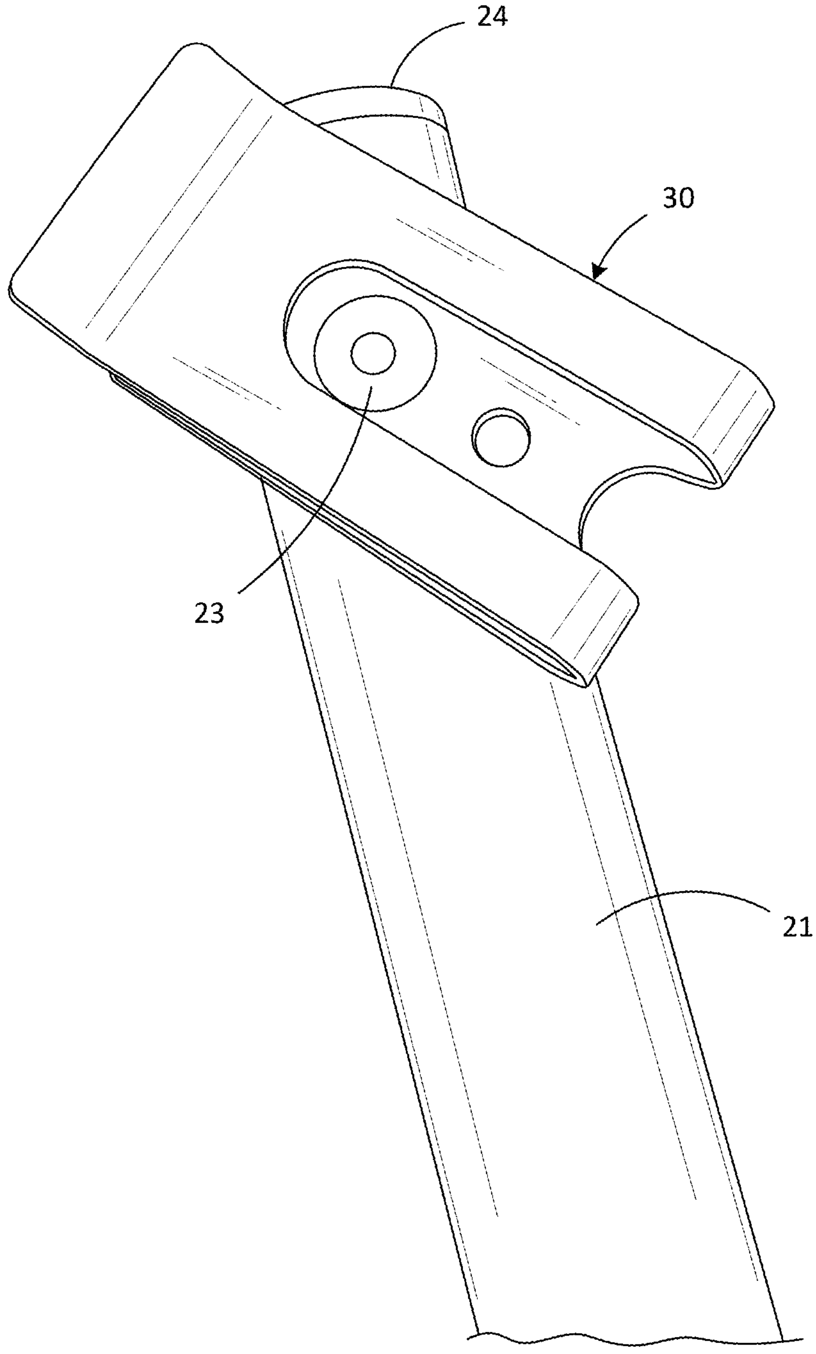
FIG. 3A is a plan view of swivel clip mounted on adjustable leg, shown in position swiveled at slightly with respect to the adjustable leg.
Figure 4:
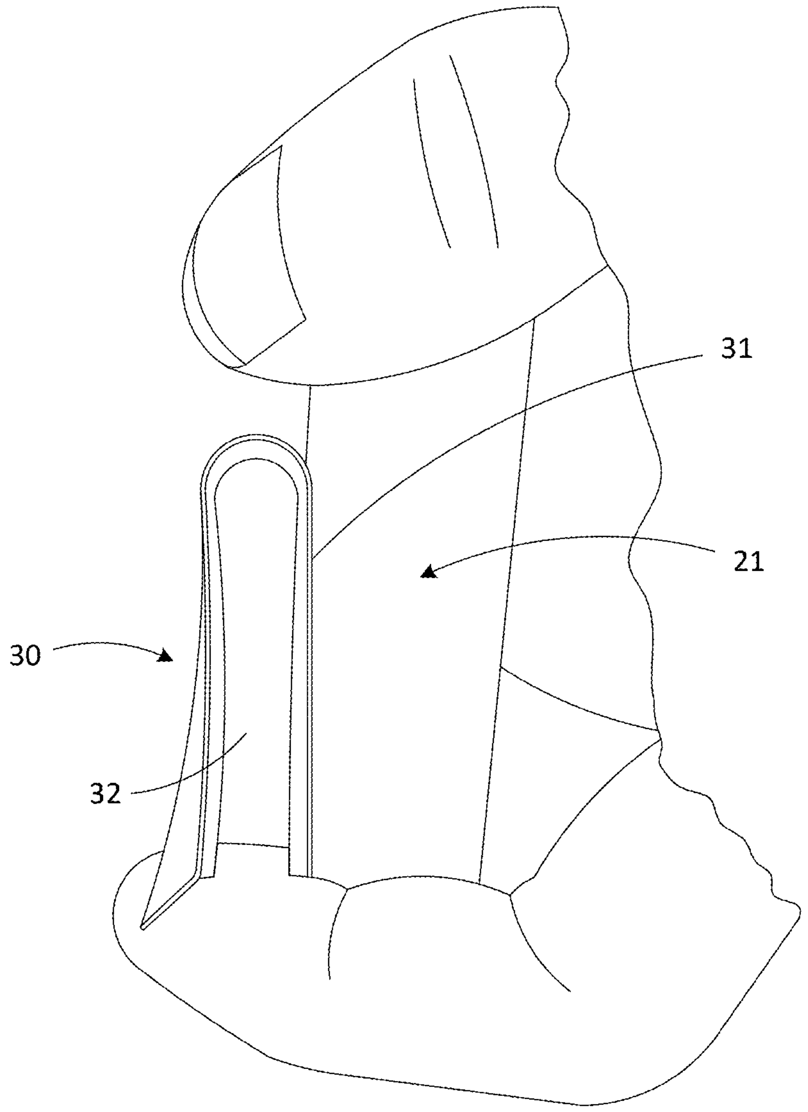
FIG. 4 is a side view of swivel clip mounted on adjustable leg, with the outer leg of the clip being forced apart from inner leg of clip.

Clip 30 is rotatably mounted on a rivet 23 which is secured to inner telescoping sleeve 21. Clip 30 is free to swivel to different positions as shown by comparing FIGS. 3 and 3A. Clip which can be clipped downwardly over a belt such that when the patient puts said under arm rest under his or her arm, his or her upper torso is stretched somewhat or partially unweighted. Clip 30 is generally "U" shaped, having an inside mounted leg 31 and a springy clamping leg 32. FIG. 4 is a close up clip 30 with mounted leg 31 mounted on inner telescoping sleeve 21 and clamping leg 32 being held spaced apart from inner leg 31. Clip 30 can thus be clipped downwardly over a belt such that when the patient puts said under arm rest 10 under his or her arm, his or her upper torso is stretched somewhat or partially unweighted, which eases the lower back pain.

The swivel mounted clip 30 allows the clip to swivel to different positions which may be assumed by the patient to reduce the pain he or she feels when occupying a first position too long. Most people experience pain in varying different positions, often at different times.

Further, the swivel mount on clip 30 allows clip 30 to accommodate the different positions the patient might occupy in working, laying down, sitting up, standing up, and performing other routine daily functions. The fact that these can be performed in an orthopedic device 1 means that the device will continue to provide relief while the device is worn.

Figure 5:
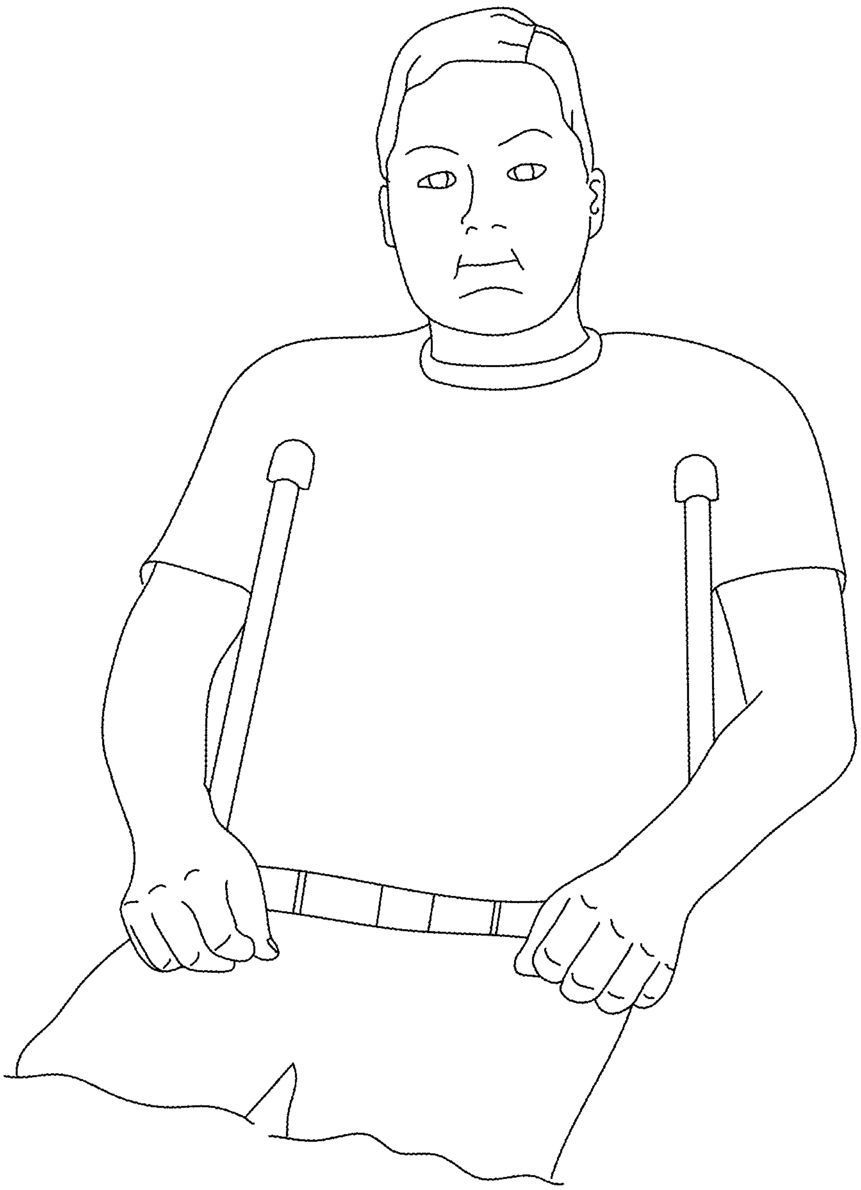
FIG. 5 shows a user sitting at a desk working while using the orthopedic device.
Figure 6:
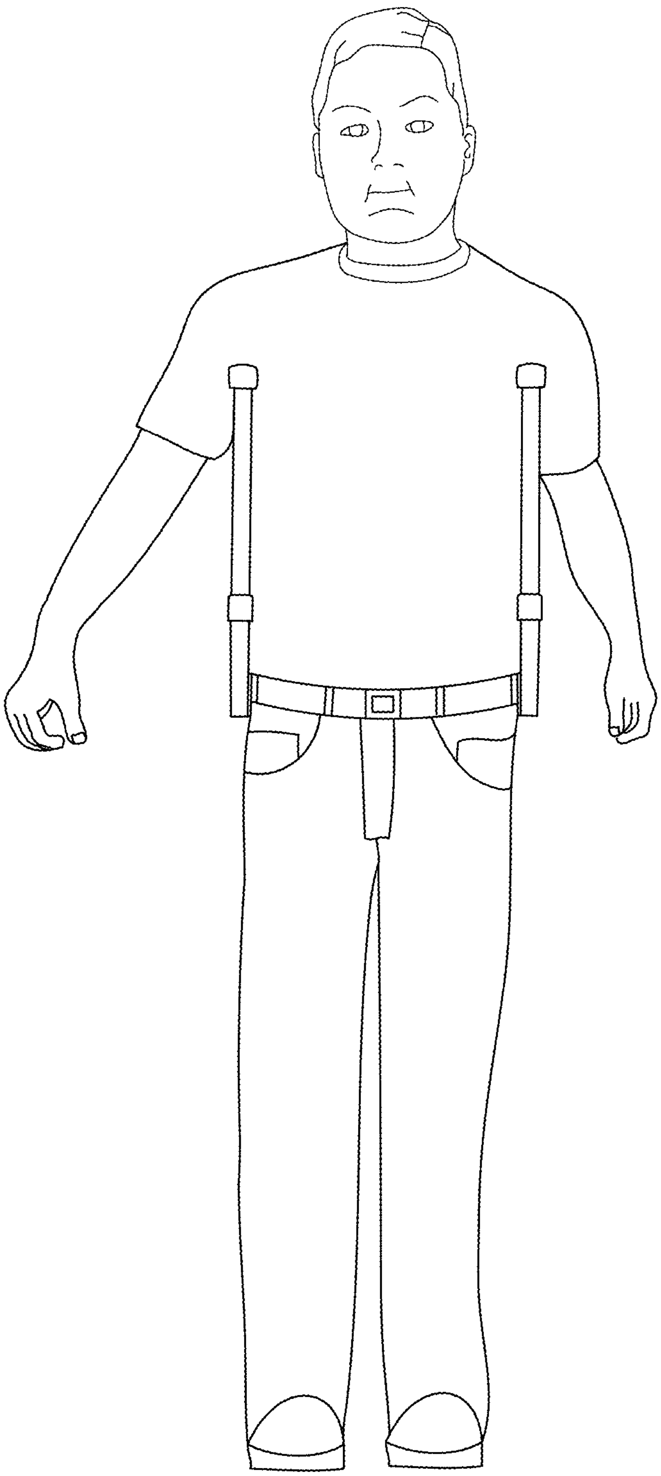
FIG. 6 sows a user being active in a standing position while using the orthopedic device.
Figure 7:
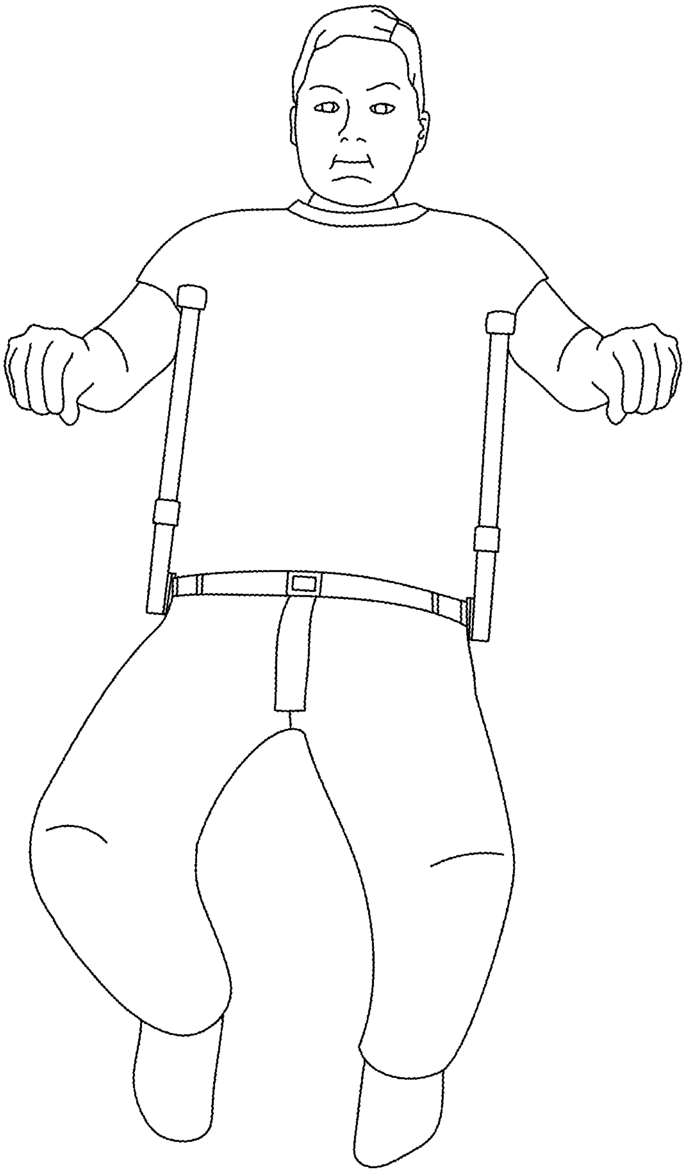
FIG. 7 shows a user laying down while using the orthopedic device.
Figure 8:
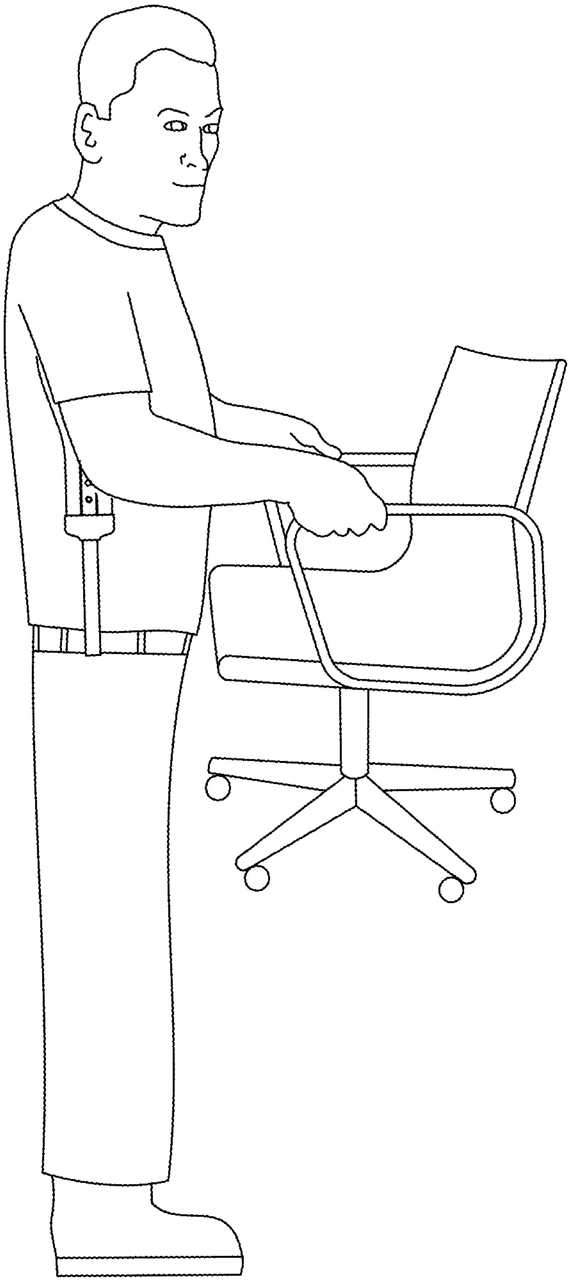
FIG. 8 shows a user lifting a chair to move it while using the orthopedic device.

For example, FIG. 5 shows a user sitting at a desk working while simultaneously using orthopedic device 1 to relieve pain. FIG. 6 shows a user being active in a standing position while using orthopedic device 1 to relieve lower back pain. FIG. 7 shows a user laying down while using the orthopedic device, and no doubt changing positions in his or her sleep. Finally, FIG. 8 shows a user lifting a chair to move it while using the orthopedic device. Further, in all of these uses, orthopedic device 1 is used while wearing clothing, but is used outside of clothing being warn.

Thus, the use of orthopedic device 1 allows a user/patient to obtain relief while maintaining an active life, and while adjusting different pain relieving positions from time to time. These and other objects and advantages will be appreciated by those skilled in the orthopedic device art, and those suffering from lower back pain.

The invention claimed is:

1. An orthopedic device having a lateral under arm rest for positioning under a patient's arm; an adjustable length leg connected to and extending downwardly from said lateral under arm rest; and a swivel clip rotatably mounted on an outside of said adjustable leg near its terminal end; said swivel clip being configured to be clipped downwardly over a waist belt on a patient; said adjustable length leg being adjustable to extend approximately the length of a patient's upper torso from the underarm to the waist of a patient at a point where, when the patient puts said under arm rest under his or her arm, his or her upper torso is stretched somewhat and partially unweighted; said swivel clip facilitating a patients use of said orthopedic device in a variety of relief giving positions, such as sitting, standing, laying down, standing, or laying on a side by swiveling to different angular positions relative to said belt to accommodate such varying relief giving positions.

2. The orthopedic device of claim 1 in which said swivel clip is rotatably mounted on a rivet which is secured on the outside of said adjustable leg near its terminal end; said swivel clip being generally downwardly opening "U" shaped, having a first leg opposed to a springy clamping leg such that said swivel clip such can be clipped downwardly over a belt and swivel to different angular positions relative to said belt to accommodate said varying relief giving positions.

3. An orthopedic device having a lateral under arm rest for positioning under a patient's arm; two spaced struts connected to said under arm rest at points spaced from each other and extending downwardly and inwardly towards each other from their connection to said arm rest; each said strut terminating at its respective connection to a strut receiving housing; said strut receiving housing also housing a fixed length outer sleeve which is mounted at its top in approximately a center of the under arm rest and at its bottom to said strut housing, between terminating ends of said struts; said fixed length outer sleeve being approximately the length of an upper torso of a user of said orthopedic device from the underarms to the waist of said user; said fixed length outer sleeve telescopically housing an inner telescoping sleeve of approximately the same length of the fixed length outer sleeve such that said outer and inner sleeves comprise an adjustable length supporting leg; said inner telescoping sleeve being adjustably telescoped out of said fixed length sleeve to change the effective length of said leg to accommodate use of said orthopedic device in a variety of orthopedic pain relieving positions; a terminal end swivel clip rotatably mounted on said telescoping sleeve near its terminal end; said swivel clip being configured to be clipped downwardly over a waist belt on a patient and being swivel able to facilitate a patient's use of said orthopedic device in a variety of relief giving positions, such as sitting, standing, laying down, standing, or laying on a side by swiveling to accommodate said varying positions.

4. The orthopedic device of claim 3 in which said swivel clip is rotatably mounted on a rivet which is secured on the outside of said inner telescoping sleeve near its terminal end; said swivel clip being generally downwardly opening "U" shaped, having a first leg opposed to a springy clamping leg such that said swivel clip can be clipped downwardly over a belt and swivel to different angular positions relative to said belt to accommodate said varying relief giving positions.

5. A method of relieving lower back pain in a patient in various body positions and activities in which it occurs comprising: selecting two orthopedic devices, each having a lateral under arm rest for positioning under a patient's arm; an adjustable length leg connected to and extending downwardly from said lateral under arm rest; and a swivel clip rotatably mounted on an outside of said adjustable length leg near its terminal end; said swivel clip being configured to be clipped downwardly over a waist belt on a patient; placing each of the patient's arms over said lateral arm rest of each orthopedic device on each of patient's sides, clipping each of said swivel clips to a patient's waist belt, and adjusting said of each adjustable length leg to extend to a point where, when the patient puts said under arm rests under each of his or her arms, his or her upper torso is stretched somewhat and partially unweighted; adopting various pain relief giving positions by allowing said swivel clip to swivel to different angular positions relative to said belt to accommodate such varying relief giving positions.

6. The method of relieving lower back pain of claim 1 in which the patient adopts a seated position while using said orthopedic devices.

7. The method of relieving lower back pain of claim 1 in which the patient adopts a standing position while using said orthopedic devices.

8. The method of relieving lower back pain of claim 1 in which the patient adopts a laying down position while using said orthopedic devices.

9. The method of relieving lower back pain of claim 1 in which the patient adopts an object lifting position while using said orthopedic devices.

* * * * *